US006652481B1

(12) United States Patent
Brown et al.

(10) Patent No.: US 6,652,481 B1
(45) Date of Patent: *Nov. 25, 2003

(54) HYGIENIC SALIVA COMPENSATION DEVICE WITH IMPROVED HANDHELD AND INTRA-ORAL COLLECTION DEVICE

(75) Inventors: Carrie Brown, Dallas, TX (US);
Lorton Trent, McKinney, TX (US);
Jack Atkinson, Southlake, TX (US);
Janet H. Allaire, Charlottesville, VA (US); Eric Frische, Chandler, AZ (US);
Richard Adams, Plano, TX (US)

(73) Assignee: Innovative Human Services, Inc., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/565,169

(22) Filed: May 3, 2000

Related U.S. Application Data

(63) Continuation-in-part of application No. 09/437,910, filed on Nov. 9, 1999, now abandoned, which is a continuation-in-part of application No. 09/012,936, filed on Jan. 24, 1998, now Pat. No. 5,980,498.
(60) Provisional application No. 60/038,444, filed on Feb. 19, 1997.

(51) Int. Cl.[7] .............................. A61M 1/00; A61B 5/00; A61B 81/00
(52) U.S. Cl. ........................ 604/35; 600/573; 604/327
(58) Field of Search .................. 604/327, 315, 604/541, 268, 317, 35; 600/573, 532, 366, 582; 422/101; 128/204.21, 203.27

(56) References Cited

U.S. PATENT DOCUMENTS

| 4,114,605 A | 9/1978 | McGhee et al. | |
| 4,201,212 A | 5/1980 | Bradley | |
| 4,417,874 A | * 11/1983 | Andersson et al. | 433/96 |
| 4,635,488 A | 1/1987 | Kremer | |
| 4,768,238 A | 9/1988 | Kleinberg et al. | |
| 4,813,931 A | 3/1989 | Hauze | |
| 4,817,632 A | 4/1989 | Schramm | |
| 4,834,110 A | 5/1989 | Richard | |
| 5,045,074 A | 9/1991 | Satterfield et al. | |
| 5,050,616 A | 9/1991 | Wolff et al. | |
| 5,110,557 A | 5/1992 | Brown et al. | |
| 5,134,994 A | * 8/1992 | Say | 128/200.24 |
| 5,143,087 A | 9/1992 | Yarkony | |
| 5,260,031 A | 11/1993 | Seymour | |
| 5,268,148 A | * 12/1993 | Seymour | 422/100 |
| 5,271,902 A | * 12/1993 | Sakka et al. | 250/577 |
| 5,281,108 A | * 1/1994 | Brooke | 417/395 |
| 5,380,492 A | 1/1995 | Seymour | |
| 5,393,496 A | 2/1995 | Seymour | |
| 5,441,410 A | * 8/1995 | Segerdal | 433/93 |
| 5,494,646 A | * 2/1996 | Seymour | 422/101 |
| 5,688,121 A | * 11/1997 | Davis | 433/91 |
| 5,720,299 A | * 2/1998 | Theodoru | 600/573 |
| 5,980,498 A | * 11/1999 | Brown et al. | 600/573 |

* cited by examiner

Primary Examiner—Weilun Lo
Assistant Examiner—Linh Truong
(74) Attorney, Agent, or Firm—Haynes and Boone, LLP; John W. Montgomery

(57) ABSTRACT

A portable saliva compensation device is provided with a portable carrying case holding a vacuum pump, and a portable power supply for providing power to vacuum pump. A programmable electrical control circuit is connected to the portable power supply and the pump. A saliva collection device is provided having a portion thereof positionable inside user's mouth for collecting excess saliva and conveying it to a hollow tube connecting between the saliva collection device and the vacuum pump. An activation operably coupled to the electrical control circuit to activate the vacuum pump when saliva is to be collected from the user's mouth. This draws the saliva from the collection device through said hollow tube and into a collection reservoir.

15 Claims, 14 Drawing Sheets

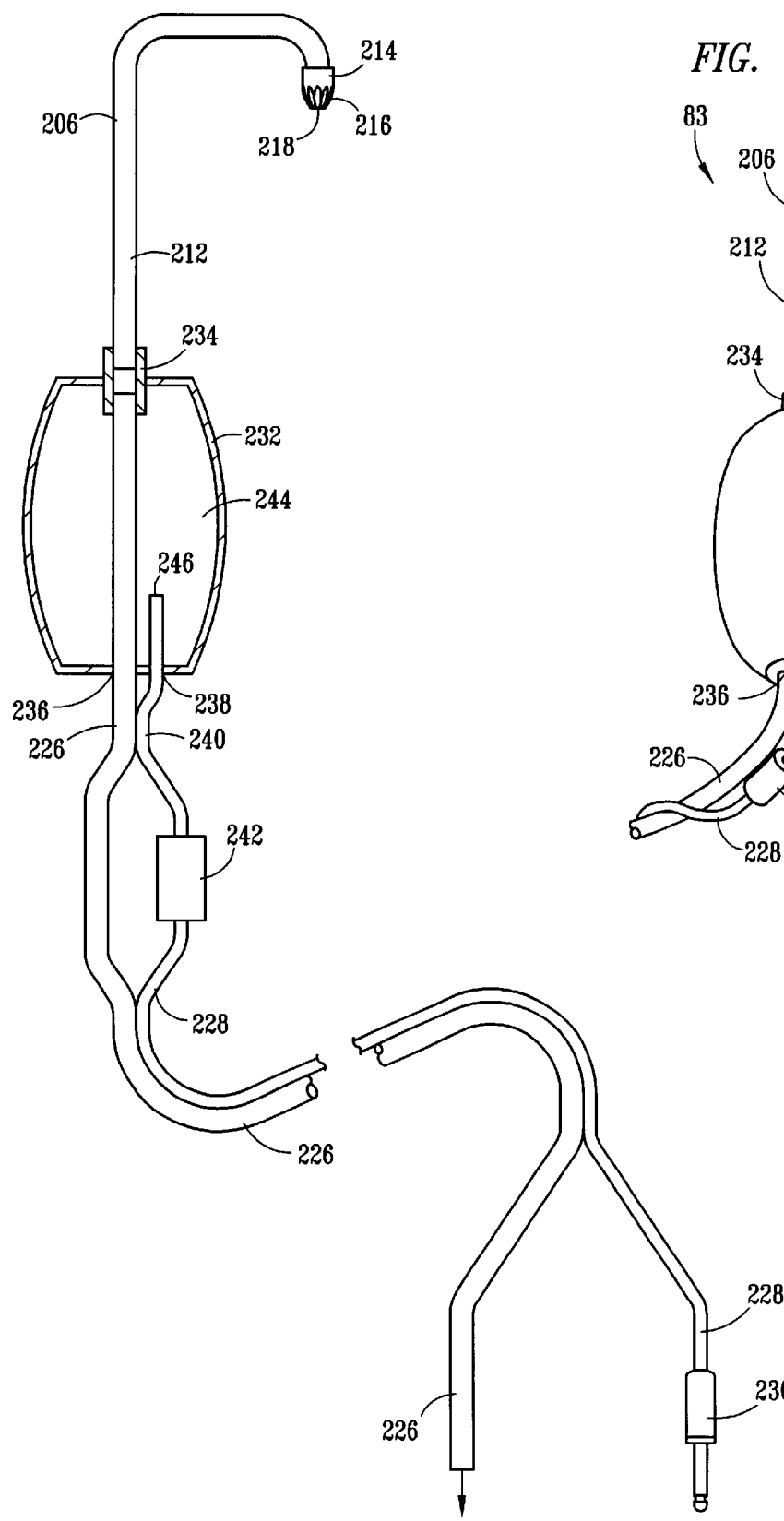
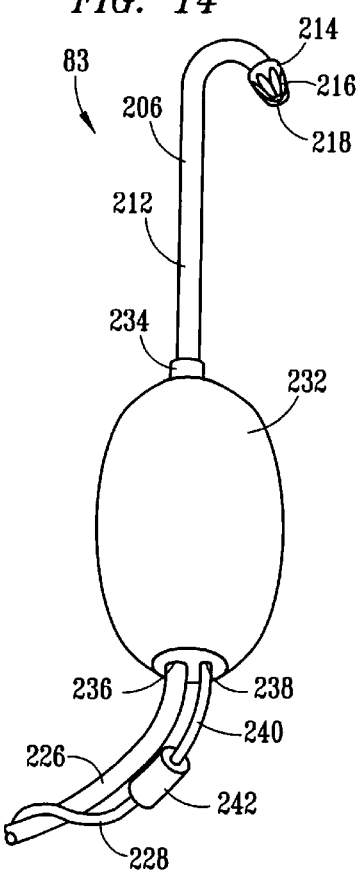
FIG. 15
FIG. 14

HYGIENIC SALIVA COMPENSATION DEVICE WITH IMPROVED HANDHELD AND INTRA-ORAL COLLECTION DEVICE

RELATED APPLICATIONS

This application is a continuation-in-part of U.S. patent application Ser. No. 09/437,910, Nov. 9, 1999, now abandoned that was a continuation-in-part of U.S. patent application Ser. No. 09/012,936, Jan. 24, 1998 and issued as U.S. Pat. No. 5,980,498 on Nov. 9, 1999 that is a continuation-in part and conversion of provisional application filed under 37 C.F.R. §1.53(b)(2), Provisional Patent Application No. 60/038,444, filed Feb. 19, 1997, upon which Applicant relies for priority and which are incorporated herein by reference for all purposes.

TECHNICAL FIELD OF THE INVENTION

The present invention relates to a device for use by individuals having conditions, resulting in excessive saliva, improper swallowing functions or other conditions or disorders resulting in uncontrolled drooling. Particularly this relates to a portable hygienic saliva compensation device and method.

BACKGROUND OF THE INVENTION

Drooling is abnormal for people beyond the age of toddlers. For some people with a variety of neurological conditions, drooling is a chronic problem which cannot be remedied by standard intervention methods. There is no definitive research data on the number of people with drooling problems, but the literature estimates that ten percent (10%) of all people with cerebral palsy have unwanted drooling. Individuals with conditions such as head injury, Amyotropic Lateral Sclerosis, and other degenerative neurological diseases can also have a drooling problem.

Previously, there has not been an acceptable device for reliable collection of saliva overflow during normal activities of a person with a drooling problem and that includes research and training capabilities. Without a truly portable and convenient apparatus for the collection of saliva, accurate data related to this problem cannot be easily obtained. Not only would a device be beneficial for people with excess saliva overflow but also reliable collection of saliva overflow is essential for determining the effectiveness of various intervention strategies. Such a device could also be useful as a research tool for physicians and other clinicians in their research to determine the effectiveness of different behavioral, pharmaceutical, and surgical techniques and intervention in dealing with this problem. Moreover, a device useful for clean, safe hygiene and research, and a device that is also useful as a training tool to assist in teaching people better behavioral techniques for swallowing and other saliva compensation activities is desirable and has not previously been provided.

SUMMARY OF THE INVENTION

Applicants' invention addresses many of the foregoing needs by providing a modularized, assistive technology hygienic saliva compensation device which is portable by the user and which the user can operate to clean his or her mouth, lips, chin and shirt front of unwanted saliva.

It is the object of the present invention to provide a portable hygienic saliva compensation device. Such a device is desirably discreet, aesthetically acceptable to the user, quiet and reliable.

It is the further object of the invention to provide a hygienic saliva compensation device which is modularized and portable so that it can be carried by the user in a backpack, or fanny pack, or attached to a wheelchair or moveable from one chair to another or from one table to another.

It is the further object of the present invention to provide a device which functions as a vacuum for saliva overflow, collects saliva drool for disposal and/or measurement purposes.

It is the object of the present invention to provide a saliva compensation device which is hygienic and easy to clean, simple for users and for care givers to operate, is nonirritating to the skin, and helps reduce odor problems often associated with excessive drooling.

It is the further object of the present invention to comfortably accommodate natural movements of the user including head, neck, torso, and body movements.

It is the further object of the present invention to provide a saliva compensation device which is designed for conducting research and also for training users to swallow, including variable timing devices and a flexible, embedded cuing system.

It is the further object of the present invention to provide a device useful for clinicians and researchers to determine differences in the amount of drool collected due to different types of clinical or physical interventions by monitoring the amount of saliva overflow collected in a container.

It is an object of the present invention to provide integrated software and hardware in a saliva compensation device to collect data for later analysis on a variety of variables, including natural activities of the user, and such as head tilting and swallowing, the number and type of cues given to the user, and number of times and the duration that the vacuum pump is activated. The software and hardware work together to determine and to indicate when the drool collection container or reservoir reaches a full condition.

It is further an object to provide a device with capabilities of being preprogrammed with a computer, of recording operations data in a portable unit, of providing a convenient downloading for analysis in a personal computer (PC) through a data communication port, such as an RS-232 serial port, a parallel port, or an infrared communication port.

It is another object to provide a portable device having a programmable, integrated circuit (PIC) capable of receiving downloaded programming instructions for operation, cuing, monitoring of device functions, monitoring of physiological conditions and physical actions of a user. Uploading Uploading and downloading of instructions from software or another machine, such as a personal computer, is advantageous for research, teaching, and controlling or compensating for excessive salivation.

It is the further object of the present invention to provide an electromechanical, computerized device using various molded silicone parts, molded plastic parts, flexible tubing, flexible wiring, a lightweight pumping unit, a portable power source, and a pre-manufactured or injection-molded carrying case for holding electronics, batteries, pumps, containers and other components in a portable unit. The modular construction preferably allows for the selection of one or more of several types of collection units. The device is selectably useable and programable with clinical, teaching and research software.

In one embodiment the device may be manufactured in a configuration primarily for use by the buyer. Such a configuration may include the basic pump, collection unit and carrying case. The essential user unit would preferably include a pump, a collection bottle, a battery, control electronics and one or more collectors. For example, the user unit may advantageously include capabilities of accepting more than one of several types of collection units. It would be small and lightweight and need not include research or training capacity. The user would typically be provided with a shirt collection unit, a face collection unit, a wrist collection unit, a handheld collection unit and/or an intra-oral collection unit. Automatic activation, user switch or user button activation is provided. The unit may have a switch or a combination of switches. Types of switches include a user switch to turn the pumping unit "on" and "off," an automatic resistance sensor to detect the presence or absence of saliva in a collector, a programable "time-out" function to turn on at a predetermined interval to automatically turn on the pumping unit for a predetermined time. The absence of saliva in the collector may turn the pump off or a preselected pumping duration can automatically turn the pump off.

In a second embodiment a clinical saliva compensation unit is configureable having clinician activation, as well as multiple input and output connectors to electronic control circuitry. The multiple input and output connectors are convenient and useful for training and research. An onboard Programable Integrated Circuit or PIC is programmable using a PC and data transfer technology. A user can be monitored and evaluated by a clinician and a software module can be provided for data collection and storage. The data can be transferred to other computer devices such as PCs for reconfiguration, data download, analysis, training and/or for research. The timeout function mentioned above may be linked to a sensor of physical activity, such as swallowing, to reset the timer, to otherwise alter the programable automatically-timed pumping activation and to be linked to training activities. Interconnection of any or all of the pump activation mechanisms with optional swallowing detectors is useful for determining whether the pumping is required or whether the pumping duration can be reduced because the user has recently swallowed. Advantageously, programming can be uploaded to the PIC from a clinician's PC and data can be collected and downloaded to the PC from onboard data collection modules.

In a particularly useful clinical device, the main unit has the two saliva collector ports, clinician switch, user switch, two device activation connectors, an X-10 activation, a speech input/output, an RS-232 link, connector for a swallow frequency device, head tilt switch connector, two sensitivity switches, a power on/off button or switch, a PIC, a collection bottle, batteries and a solenoid valve for controlling a vacuum valve that governs the steering of the vacuum to an appropriate saliva collector.

BRIEF DESCRIPTION OF THE DRAWINGS

These and other objects and advantages will be more fully understood with reference to the following detailed description, claims and drawing figures in which like numerals represent like elements and in which:

FIG. 14 is a perspective view of another embodiment of a handheld oral collector adapted for connection to the portable saliva collection device;

FIG. 15 is a schematic partial cross-section view of the handheld oral collector of FIG. 14.

DETAILED DESCRIPTION OF THE PREFERRED EMBODIMENTS

Figure 1:
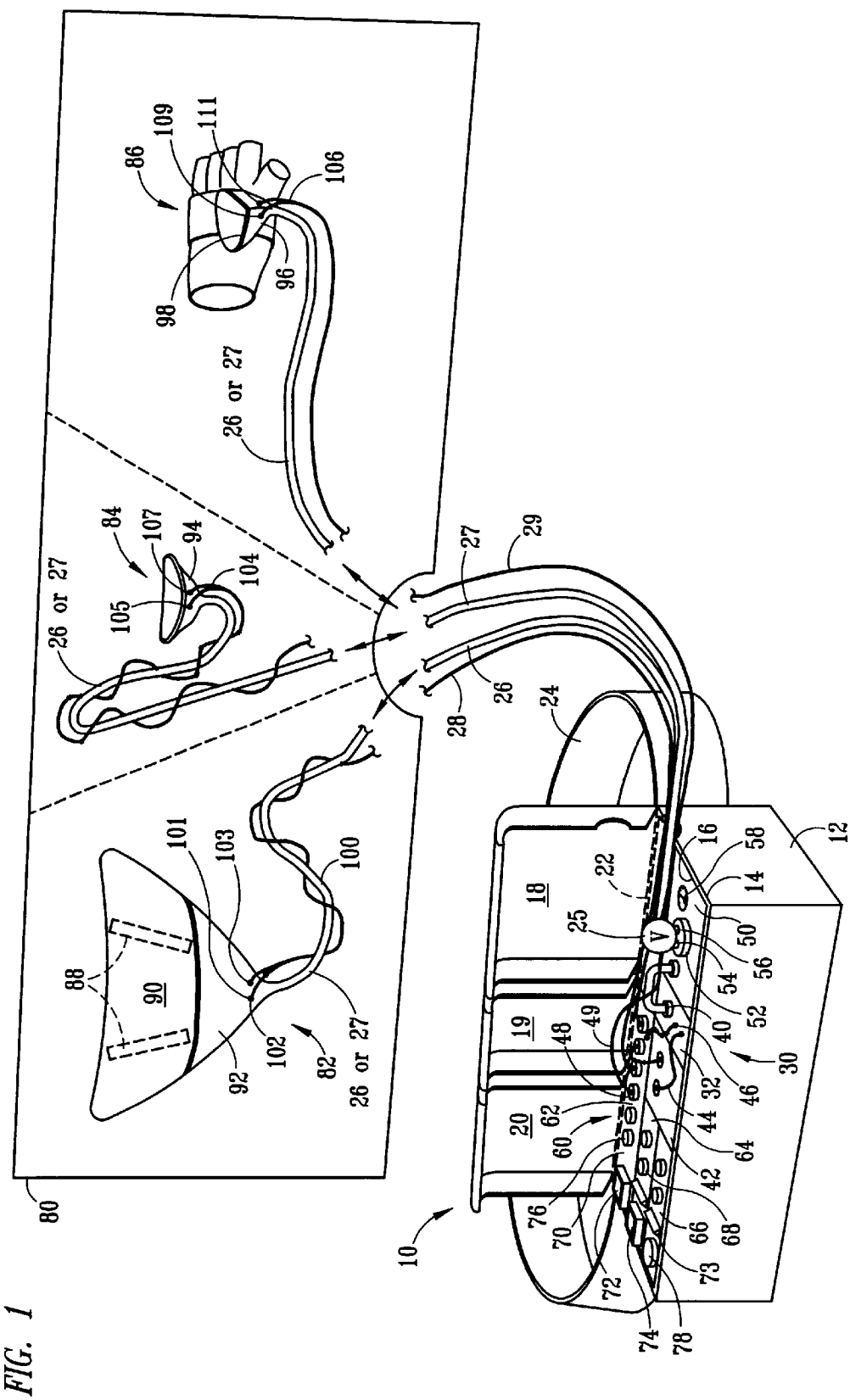
FIG. 1 is a schematic depiction of one embodiment of a portable hygienic saliva compensation device connectable to one or more of a plurality of alternative designs for a saliva collection unit, including, for example, a shirtfront unit, a face collection unit, and a wrist collection unit as shown.
Figure 2:
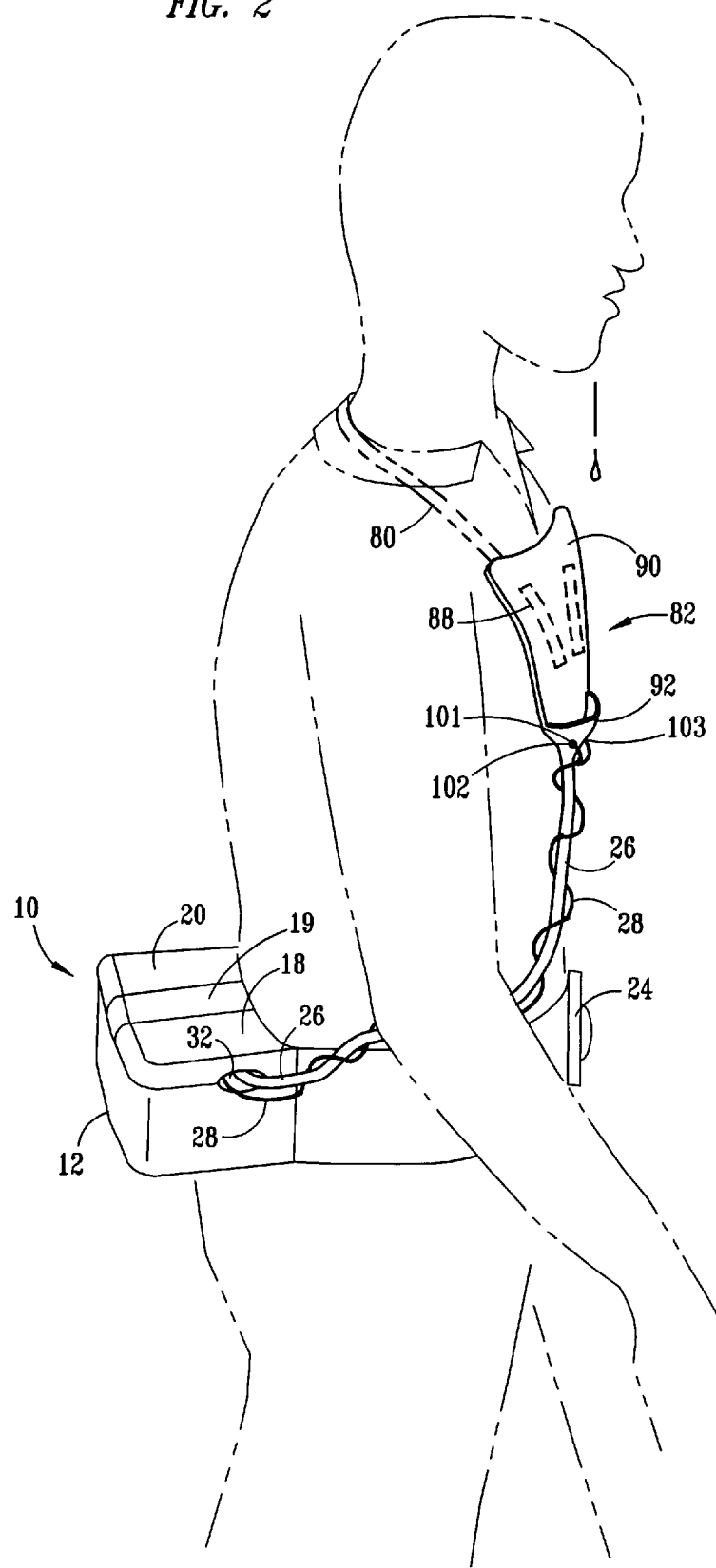
FIG. 2 is a schematic depiction of a portable fanny pack embodiment with a shirtfront collection unit in place on a user (shown in phantom lines)
Figure 3:
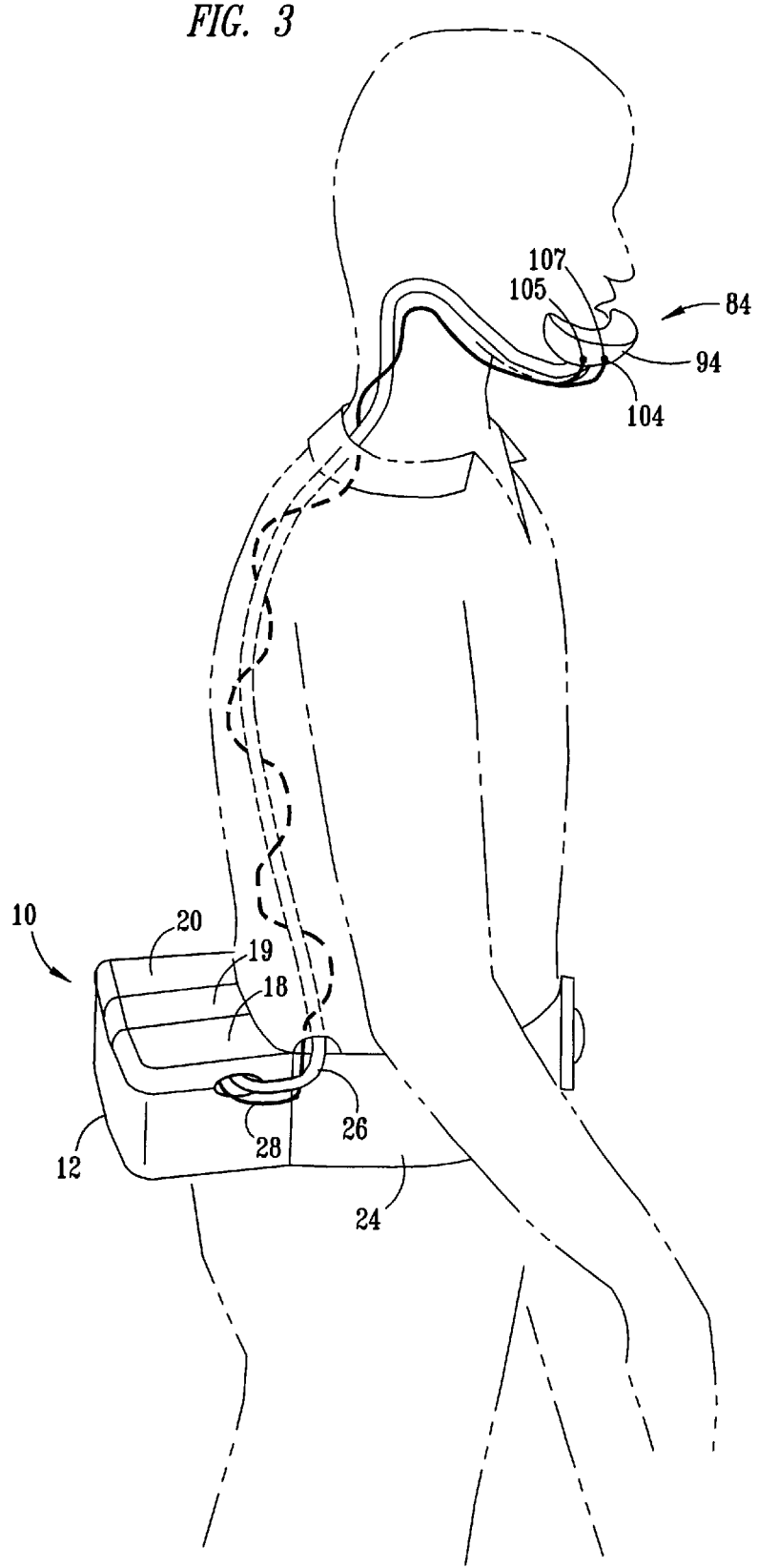
FIG. 3 is a schematic depiction of an embodiment of the invention which is a portable fanny pack modular unit and a face collection unit adhered below the lower lip of the user (shown in phantom lines)
Figure 4:
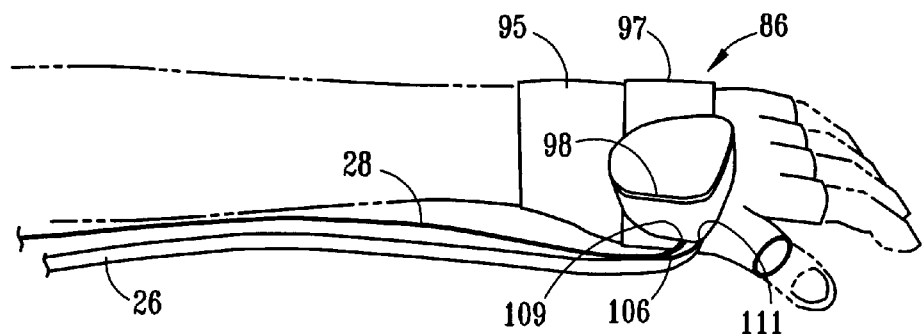
FIG. 4 is a partial schematic side view of a wrist collection unit.
Figure 5:
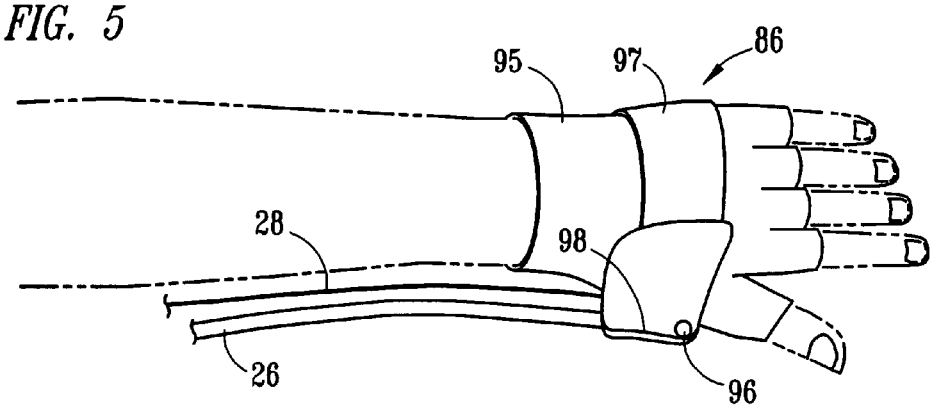
FIG. 5 is a schematic top view of the wrist collection unit of FIG. 4.

FIG. 1 is a schematic depiction of a portable hygienic saliva compensation device 10 connectable to two of three alternative designs for a saliva collection unit schematically depicted in box 80 as shirtfront unit 82, face unit 84 and wrist collection unit 86. The use of each of the selectable collection units 80 will be more fully understood and more fully described below with reference to FIGS. 2, 3 and 4 in which FIG. 2 is a schematic depiction of a portable fanny pack embodiment with a shirtfront collection unit in place on a user (shown in phantom lines); FIG. 3 is a schematic depiction of a portable fanny pack embodiment modular unit connected to a face collection unit adhered below the lower lip of the user (shown in phantom lines); FIG. 4 is a partial schematic side view of a wrist collection unit. FIG. 5 is a schematic top view of the wrist collection unit of FIG. 4.

Referring again to FIG. 1, the hygienic saliva compensation device includes a carrying case 12, the exterior of which may be made of any number of protective outer material such as fabric, polymeric material, metallic material constructed to provide an interior space 16. Preferably the carrying case is formed of a sewn fabric material having a structural sheet material such as cardboard or polycellular material or Styrofoam interposed there along to provide both structure and protection for the components contained within the interior 16. In the embodiment depicted a three-piece cover including a reservoir cover 18, batteries compartment cover 19 and an electronic cover 20 are provided pivotally-hinged or flexibly attached along a top edge along the top edge of the carrying case. A support device 24, which in the embodiment shown is a belt 24, is used for conveniently removably securing the carrying case to the user for convenient unencumbered portability. A suction tube 26 and sensor cable 28 which extends from the side of the carrying case and connects to various internal components at one end and connects to one of the selected collection units 82, 84 or 86 at the other end. Suction tube 26 connects to container 50 through inlet cap 52 and first inlet port 54 extending through the inlet cap. Pump 32 of the pump unit 30 receives power from power cable 44 connected to battery 42. The collection container 50 is sealed and capable of withstanding at least a partial vacuum. Pump 32 of pump unit 30 connects to container 50 through a vacuum tube 40 to create a vacuum in container 50 to suction saliva through suction tube 26. In a preferred embodiment, a second suction tube 27 also connects to the container 50 at second inlet port 56 and for suctioning saliva from a second one of the selectable collector units 82, 84 and 86. Saliva is suctioned through the second suction tube 27 and into the collection reservoir through cap 52 and second inlet tube 56. A vacuum route solenoid valve 25 is provided to select which suction tube receives the vacuum and thus which collector unit will be vacuumed. A vacuum route selection switch 48 communicates with the valve 25 to selectably determine and control the valve position. For example, detection of saliva in one collector 82 with one sensor 102, activates the valve 25 to the proper position to vacuum fluid from that collector 82. Detection of saliva by another sensor 104 or 106 activates the valve 25 to the proper position to vacuum fluid from the associated collector 84 or 86, as the case may be.

Sensor cable 28 extends along with tube 26 and, if an additional collector/sensor is in place, sensor cable 29 extends with tube 27 from the collection unit interconnecting with one or more sensor switches 102, 104 or 106, each correspondingly attached to the lower apex of a funnel portion 92, 94 or 96 of each of the collector units 82, 84 or 86 respectively. The sensor cable 28 is selectably connectable to one of the sensors 102, 104 or 106 and thereby communicates the input from the collector to the control unit 60. Detection of moisture at an apex of a funnel of a collector unit provides a signal to the first circuit panel 62 of the control module 60 at one of a plurality of input connectors 70 and the vacuum route valve is activated to the proper position. The first circuit panel 62 is also interconnected to receive power from a portable power supply such as main rechargeable battery 42 or, in the alternative, includes its own separate battery (not shown) and provides programmable control of the pump unit 30 through control wire 46. Pump 32 of pump unit 30 is activated and the vacuum route valve 25 is positioned upon the receipt of a signal from the particular sensor switch 102, 104 or 106 as is selectably attached at the opposite end of sensor cable 28 at any given time or can be activated through clinician switch or timing function.

Control unit 60 also includes a manually activatable switch 68 by which the pump may be turned "On" or "Off" by the user or clinician. It will be understood that while switch 68 is depicted attached on the first circuit panel 62, it may also be a remotely operated switch positioned in a location convenient to the user such as on a handheld remote switch by which the pump 32 may be turned "On" or "Off" by the user to remove saliva from the collection unit as required even in advance of sufficient accumulation to activate the sensor switch 102, 104 or 106. Inadvertent failure of such automatic sensor switch can also be accommodated by such a manual dactivation switch or automatic vacuuming override. The components are connected so that one or two saliva collectors are attached to a vacuum route valve 25. The vacuum route valve attaches to the collection bottle 50. The pump attaches to the top of the collection bottle. A given saliva collector sensor, in the presence of saliva, will activate the pump to create a relative vacuum in collection bottle 50 and also to direct the vacuum, via the vacuum route valve, to its parent saliva collector. The pump sucks air out of the collection bottle, such that a vacuum is created, such that a vacuum route valve is connected via tubing to the collection bottle, such that this route valve connects to one or two saliva collectors, and such that this route valve governs which saliva collector receives the vacuum.

A plurality of input connectors 70 allow for selectable connection of multiple sensor wires and/or other sensor wires or input as from a clinical technician training console or from other sensors detecting physical or physiological activities of the user. In a preferred embodiment, the control module 60 also includes a third modular panel 64 for user cuing and a second modular panel 66 for data recordation. Additional features such as preprogrammed cuing of user activities or preprogrammed recordation of selected physiological activities of the user are thus provided to enhance the complete utility of the saliva compensation device. The basic control module also includes basic mechanisms for cuing or signaling the user to undertake certain predetermined activities and for signaling the use of the condition of the unit such as a LED light 72 provided to signal a pump "on" condition. LED light 73 (see also 136 in FIG. 6) signals a reservoir "full" condition and likewise various audible sound producing devices such as a speaker 78 (see also 171 in FIG. 6) provides remote communication capabilities or preprogrammed oral instructions to the user upon the occurrence of certain sensed conditions or events. A buzzer 76 (see also 139 in FIG. 6) or a unique sound producer 78 (see also 171 in FIG. 6), such as a "boing" sound producing device can be provided to signal predetermined different actions or conditions distinguishable from the buzzer or the audible instruction for the benefit of the user. For example, the device signals a user of a blocked saliva collection line.

The collection container 50 is constructed of a durable, rigid, lightweight material. It is self-contained, sealable to maintain a vacuum, and sufficiently strong to avoid collapsing. The container 50 is constructed to be removable from carrying case 12 to provide adequate volume capacity for collecting saliva of a particular user during a predetermined period. The collection container 50 may have an inlet port 54 or first and second inlet ports 54 and 56 connected to vacuum route valve 25 and extending through a removable inlet cap 52 by which the reservoir may be conveniently emptied. The reservoir 60 also preferably has a level indicator 58 to detect the amount of saliva collected. Indicator 58 may be a visual graduated, transparent or translucent viewing panel, or in the alternative, may comprise a level sensing float or, in a preferred embodiment, comprises an electronic sensor device by which the control module 60 receives information concerning the level of saliva collected. The level may be detected at a full level or at predetermined increments from a first measurable amount to any of a number of preselected intermediate levels up to a full level. A substantially continuous level indication can also be provided electronically to the control unit 60. Upon reaching the full level the user will be cued or signaled to remove and empty the collection container 50 by lifting it from the carrying case, disconnecting inlet cap 52 and pouring out the contents of the container. The quantity collected can be separately and independently measured or it may be disposed of if monitoring and researching does not require additional quantity measurements. Vacuuming a cleaning solution using the same route as saliva is the method for sanitizing the unit.

Referring now to FIG. 2, a shirtfront collector 82 is depicted as removably attached to the user. Preferably, the attachment is directly attached to the user's shirtfront through double-sided adhesive tape 88 (as was depicted in FIG. 1), so that the funnel portion. 92 is presented in position below a predetermined range of positions of the user's mouth and chin. Further, a vest guard portion 90 of the shirt front collector 82 is preferably provided by which the user's shirt or chest is protected from excessive saliva. The shirtfront collector 82 addresses the problem for users with large and uncontrolled spills at random locations. Although a neck strap 80 could be used in some situations to support the shirtfront collector, it has been found preferable in most instances to avoid neck straps. In a preferred embodiment, double-stick tape 88 fastens the collector to the user's clothing without the use of a potentially cumbersome neck strap. The user whose saliva suddenly spills from the mouth in a stream is provided with convenient compensation and collection. The shirtfront collector 82 is shaped like a small trough or funnel 92 and is attached to a semi-rigid plastic vest portion or guard 90 partially encircling the front of a user's neck and positioned beneath the user's face. The guard 90 preferably has a curled edge at the sides to guide the spills into a smaller and less conspicuous collection funnel 92. Preferably a clear or transparent plastic material is used, both for the guard 90 and the funnel 92 to reduce the noticeability of the device and to facilitate aesthetic appearance. When drool spills into the funnel 92, a resistance measuring fluid sensor 102 detects liquid between two spaced-apart electrodes 101 and 103 and is activated to produce an electrical signal. The suction pump 32 is turned "on" by the signal so that the saliva will be removed by suction through the apex of funnel 92 and through tube 26. The saliva is suctioned by pump 32 and redirected into reservoir 50 (not shown in FIG. 2); the upper edge of the funnel 92 is sufficiently rigid to remain open and to present a trough directly below the user's mouth and chin for the collection of excessive saliva. The rim along the edges of the guard 90 may be constructed with a hollow channel having small perforations inwardly directly toward the surface of the vest guard 90. The hollow channel may be connected to the collection tube 26 (or 27, as shown in FIG. 1) and can be provided with a partial vacuum to suction saliva from along the edges.

In an alternative embodiment of a shirtfront collector 82, the vest guard 90 is made from a large, clear, flexible sheet of vinyl that lays against the user's shirtfront. It has an attached clear flexible vinyl funnel 92 with the collection tube and the fluid sensor at the lower apex of the funnel. The vinyl is held on the shirtfront, preferably with clear, double-sided tape. The vinyl vest guard 90 can be customized using scissors to conform to the user's body and to cover the substantially the entire typical spill area below the user's head. The vest funnel 92 collects saliva spilling down the vinyl sheet or vest guard 90 or spills falling directly from the mouth of the user into the funnel in a stream. The funnel 92 directs the saliva flow to the collection tube for suction. The upper rim of the funnel may be provided with a deformable or bendable wire portion as might be provided with an embedded metallic wire for a customization of the shape of the funnel to accommodate the particular user's range of spill area. The vinyl sheet forming the vest guard 90 and the funnel are preferably coated with a low-wetting material as, for example, the solution available under the brand name Rain-X, which increases the beading and facilitates smooth flow of the thick saliva into the collection tube. The sensor switch 102 may be constructed as a resistance switch 102 by which electrodes 101 and 103 are positioned at spaced-apart locations at the apex of the funnel 92. When a predetermined amount of saliva accumulates in the apex of the funnel 92, the resistance between the sensors will be changed, thereby signaling the presence of saliva to the vacuum. This signal is received from sensor cable 28 by the control unit 60 (as previously shown in FIG. 1). The pump preferably continues for a short time delay after the sensor no longer detects saliva to insure complete collection from funnel and tube.

With reference to FIG. 3, the selection of a face collector 84 is more fully depicted in which a face collector unit 84 is shown attached though collector tube 26 and sensor cable 28 to a control unit 60 held within a carrying case fanny pack 12. While the face collector unit may be held in position as with straps or with an operator's headset hooked around the user's ear, it has been found that a face collector 84 forming a small funnel 94 shaped like a crescent moon with the attached suction tube 26 at the lower apex 104 of the funnel 94 may be removably adhered below the user's lower lip. The silicone face collector 84 is placed on the chin under the point of a typical saliva spill. The face collector 84 is made of a clear, flexible silicone to make it less visible on the user's lip. The face unit is located below the lower lip of the user so that gravity assists pulling the saliva into the collection tube and adheres to the skin with clear, medical adhesive available under the trade name EUROBOND, or alternatively a two-sided medical tape available from 3M (Part No. S 1502 1522 and 9877). Fluid resistance sensors which sense when saliva is present, are located at the inlet opening of the collection tube 26 where it connects to the lower apex of the funnel 94. The inside of the face collector is coated with a low-wetting material such as may be obtained under the brand name Rain-X to increase the beading and facilitate flow of thick saliva to the apex 104 of the collector 94 and into the collection tube 26. The weight of the face collector 84 is preferably well under one ounce to allow it to be connected directly to the user's face.

With reference to FIGS. 4 and 5, a wrist collector unit 86 is depicted in a side perspective view in FIG. 4 and a top perspective view in FIG. 5. The wristband collector is usable by ambulatory and non-ambulatory users with good arm and wrist control. Because of the position of the funnel at the top of the wristband, subjects with cerebral palsy or with other motor control debilitating conditions may not be able to use the wrist collector in all instances. In the embodiment depicted, the wrist collector is formed of a molded plastic having the shape of a hollow quarter wedge of a pie. The wedge is about one inch deep with the collection tube (26 or 27) connected at a low point in the pie wedge which forms a small funnel. Resistance sensors (109 and 111) are also located at the low point in the funnel-formed pie wedge. The molded plastic pie wedge-shaped portion is mounted onto a wristband which may be as small as a wristwatch band or as large as a fingerless glove. A detachable material such as hook-and-loop material available from Velcro allows the collector to be selectively positioned and secured anywhere on the wristband to suit the user's needs. Preferably, the shape and size of the collector cup is selectable and formable by the clinician or the user. For example, the cup may be trimmed using scissors to conform to the user's particular physical requirements. The user can scrape left-to-right or right-to-left across the chin and lip, and the collector gathers the saliva and funnels it to the collection tube where it is suctioned. The collector is coated with a low-wetting material to increase the beading and the flow of thick saliva. The wristband and the collector are preferably opaque and can be constructed in any desired color to color combinations.

The pumping unit 30 preferably includes a vacuum pump 32 (as shown in FIG. 1) which is desirably a low volume, medium vacuum, small diaphragm pump. The diaphragm pump tends to be small and to have a long life. It is simple to repair, quiet and low cost. For example, a prototype Whisper fish pump can be modified for needed suction of approximately less than about 15 inches of mercury and about 800 ml air/min. The equivalent small battery-powered diaphragm pump with equal suction and flow may require about 200 milliamps at 6 volts.

The carrying case 12 (as shown in FIG. 1) houses the electronic and pumping hardware. It contains the pump 32, tubing 26 and 27, collection bottle 50, and sensor and switch connection jacks 70 (including two fluid sensor jacks and a user/clinician switch jack), cuing devices (X-10, two device jacks, output LEDs, low battery, container full, a four voice record and playback unit, a buzzer, and electronics (including processor, circuitry, batteries, charging circuits and charging circuit jack)). The unit is designed to assist the user in the use of the unit, in improving swallowing, and to assist clinicians in ease of programming from PCs, data collection and data and information transfer to and from other machines such as PCs. A clinician switch jack is provided as an input for functions that clinicians may wish to include in the saliva compensation device 10. The clinician switch can be programmed to give a specific cue to the user. The collection container "present" jack and the second fluid-sensing jack allow two collection devices to be used simultaneously by using the vacuum control route valve. A "line blocked" sensor or vacuum obstruction sensor 125 and alarm may also be provided. Similarly, head tilt input and swallow frequency input may also be provided to the control unit for collection, storage, research, automatic control of pump and vacuum route valve and/or feedback to the user.

Figure 6:
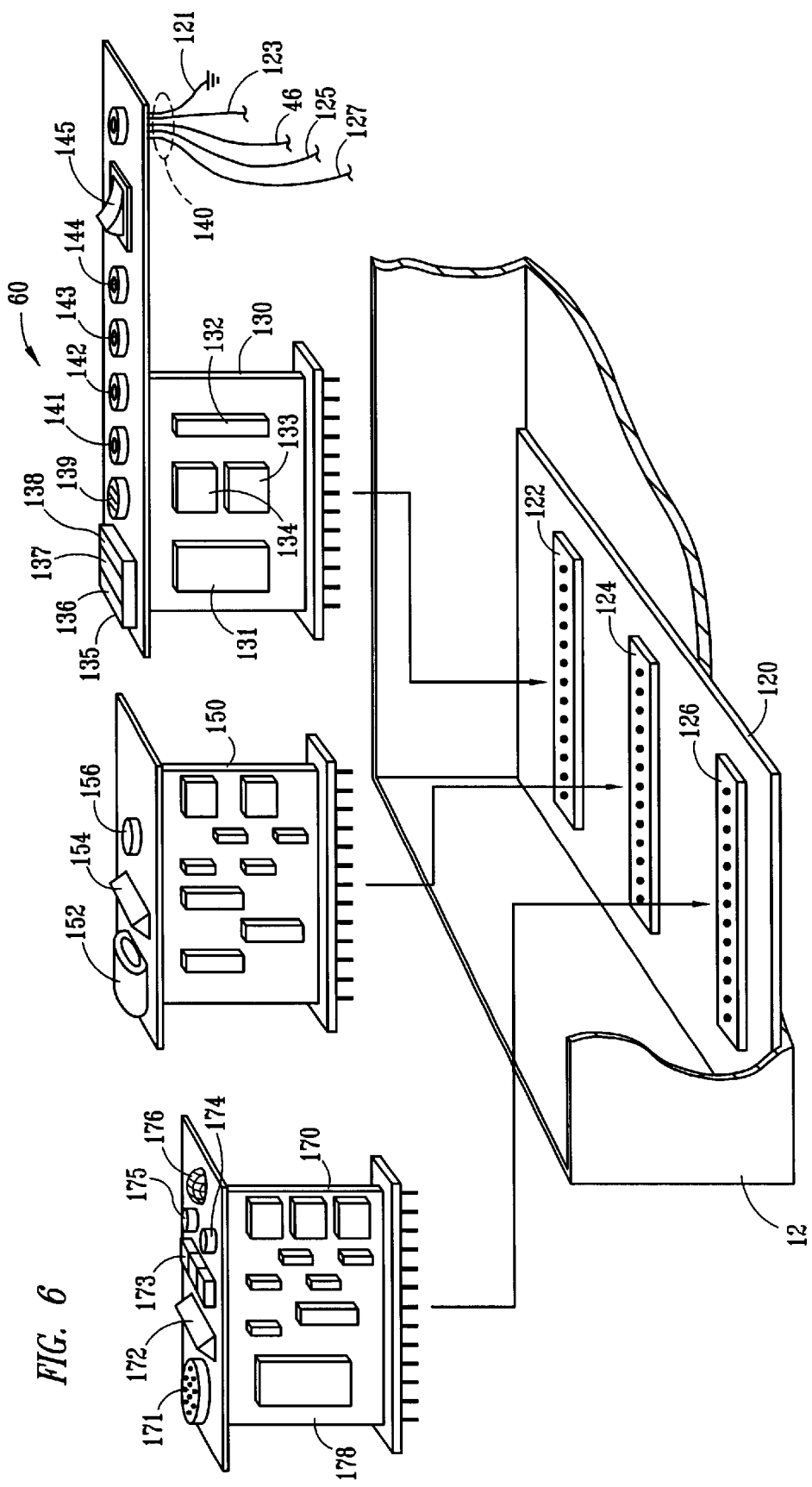
FIG. 6 is a schematic partial assembly view of electronic modular components for pin connection attachment and interconnection to a circuit board in a carrying case for interconnection with a battery power supply, activation of pump and appropriate interconnection with sensors and switching mechanisms associated with the collection units.

FIG. 6 depicts a schematic partial cutaway assembly view in which the modular components of the control unit 60 are depicted in an exploded configuration shown. A portion of the carrying case 12 is shown in cutaway view with a common power command and data busbar 120 having a pump control board 130 connector 122, a clinician's board 150 connector 124 and a voice input/output (I/O) and communications option board 170 connector 126. These connectors are attached to the common data board 120 appropriately interconnected therewith and with the pump and battery for receiving the basic pump control unit module 130, the clinician's option board 150 and the voice input/output and communications options board module 170. The basic control unit 60 contains a processor chip 131, device interface buffer 132 and plurality of driver chips 133 and 134 (as required), as well as connections for sensory input from the machine such as a ground wire 121, a battery-connected power wire 123, a pump activation line 46, a tubing obstruction sensor 125 and a reservoir full sensor 127. A LED status display 135 preferably provides indicator sections to indicate possible "error" conditions such as a jar full indicator 136, vacuum obstruction indicator 137, and a low battery indicator 138. An onboard buzzer 139 may also be present to provide a sound a tactile error signal corresponding to any one of the error signals provided by LED 135.

A variety of connection jacks are provided including a low voltage/low current jack 141 for turning on the appropriately connected remote device. A user switch jack 142 is provided to accommodate a "stereo" plug which, inserted in one side can serve as the connector to the user's pump activation switch and then connected to the reverse side serve as an external clinician's switch (useful without requiring external computer and software serial port or infrared connections). Also a first fluid sensor jack 143 is used to connect to a first fluid sensor 102, 104 or 106, and a second fluid sensor jack 144 is used for connection to a second fluid sensor switch 102, 104 or 106, depending upon the number and type of collection units 82, 84 or 86, which are being used at a given time. An on/off reset switch 145 is provided. The on/off reset switch 145 preferably is connected and preprogrammed for turning the unit "On" or "Off." When the switch is transitioned from "On" to "Off" to "On," a reset function is performed. A battery charge jack 146 is also provided to allow the battery to be recharged in the pack without removal.

The clinician's option board 150 is an add-in board which provides clinician interaction and configuration, data logging, and bi-directional communication between the clinician and the control unit, as well as between the clinician and the user. In the embodiment with the clinician's option board will have one or more communications ports 152, a board extraction handle 154 and a physiological input connection jack 156. The communications port will allow the clinician to program an onboard PIC. The port or ports may be selected from available RS 232 ports, I$^2$C ports, infrared ports and etc., capable of transmitting the programing information or transmitting the data as required.

The optional add-in voice input/output and communications options board 170 provides for selection of voice record and playback capabilities. Optional radio frequency communication capabilities advantageously allow remote control of electrical devices in the user's physical environment. For example, a lamp or a radio may be turned on to cue the user that it is time to swallow. It has been found that a system RF transmitter and RF receptor switch modules, known as the X-10 System available at Radio Shack, can be adapted to use as part of the combined invention for this purpose. The X-10 radio frequency transmission circuitry is mounted on the circuit board 178. There are no top-mounted elements for this part of the communication circuitry. The switch modules are plugged into household appliances. A voice output speaker 171 is usefully mounted on the top of the communications module to provide an audible voice playback function in the unit. A board extract handle 172 is provided for convenient insertion and extraction of the module 170. A switch (DIP) 173 is provided to select one of four voice units for record and/or playback of four different massages. A record control switch 174 is provided which may be a pushbutton 174 and a playback switch 175 which also may be a pushbutton 175 are provided. Preferably, record control switch 174 may be a spring-loaded toggle switch with record/playback/computer control positions. The record microphone 176 allows the clinician or trainer to record and play back messages for the user.

Figure 7:
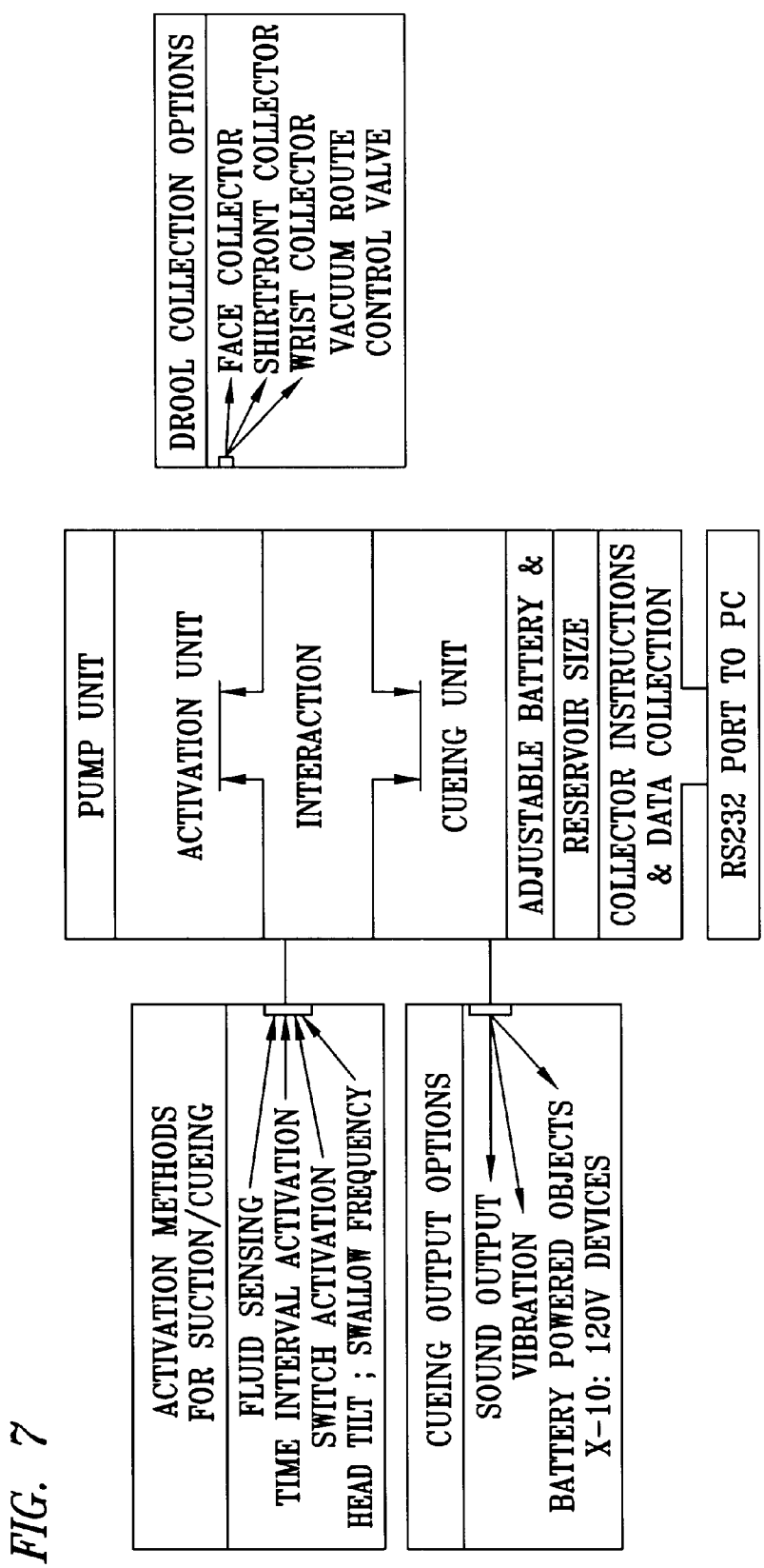
FIG. 7 is a schematic overview depiction of the modular components of the saliva compensation device, including a depiction of the pump unit, the drool collection options, including face collector, shirtfront or vest collector and wrist collector, a depiction of the activation unit and activation methods for suction cuing, including fluid sensing, time interval activation, switch activation, swallow detection or a head tilt switch and also shows a depiction of a cuing unit that may include cuing output options such as sound output, LED output, and environmental control using remote modules such as with any X-10 system, a depiction of the battery power supply, a depiction of the saliva reservoir container, and a depiction of the data collection module and the communication ports for data transfer to personal computers.

FIG. 7 is a schematic depiction of the saliva compensation device including a pump unit, a drool collection options unit, an activation unit, a cuing unit, an adjustable battery and an adjustable container size and an data collection portion with a communications port to a PC. Along with the activation unit, activation methods for suction and cuing are provided with capabilities for fluid sensing, time interval activation, and manual switch activation. A head tilt switch and a swallow frequency device and/or connections for such switches and devices may also be included. The saliva collection options associated with the activation unit and the pump unit include the face collector, the shirtfront collector, the wrist collector, a handheld collector and/or an intra-oral collector. The cuing options associated with the cuing unit and the interaction between the cuing unit and the activation unit include sound output capabilities, battery powered accessories, and X-10 radio frequey communication.

Figure 8:
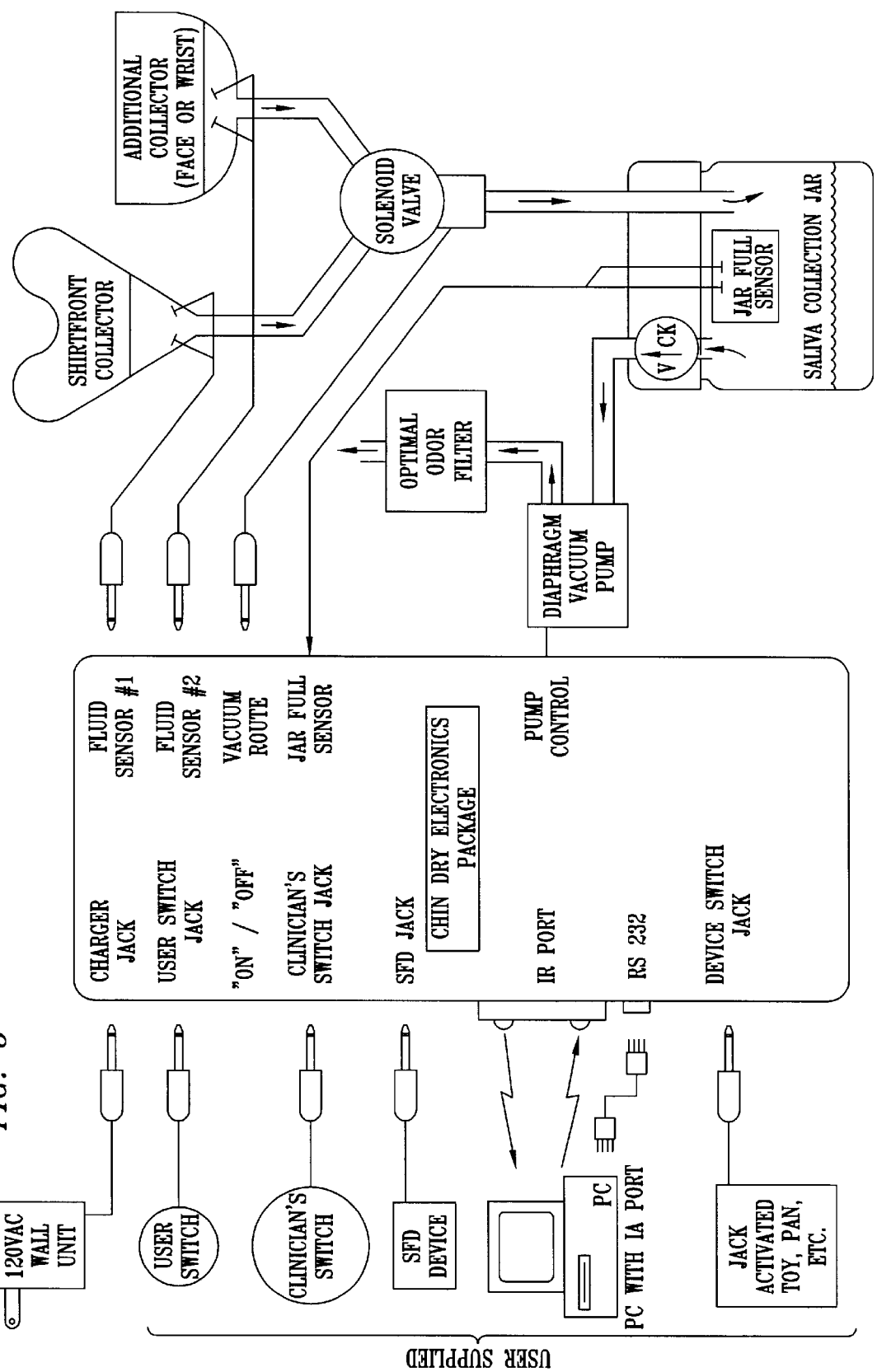
FIG. 8 is a schematic modularized system by which component parts of the saliva compensation device are detachably interconnectable with the electronic circuitry of the present invention.

FIG. 8 is a schematic depiction of one embodiment of a saliva compensation device electronic package coupled to the various alternative components.

Figure 9:
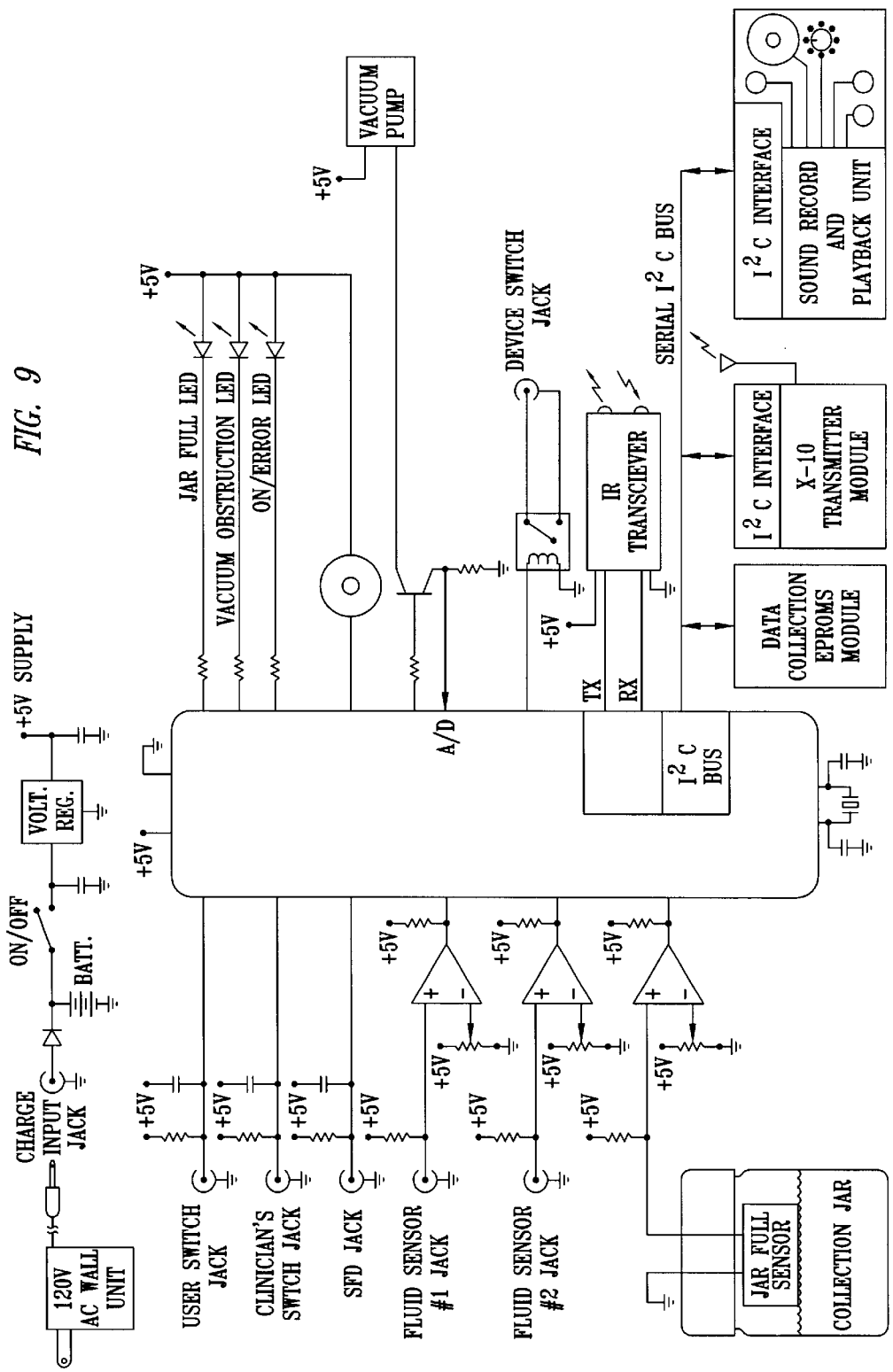
FIG. 9 is a schematic circuit diagram showing electronic circuitry interconnecting between a PIC which can be variously programmed to function as a microprocessor control chip and various components, sensors, user input, user cuing devices, pump activation, programming interface, and data transfer interfaces according to the present invention.

FIG. 9 is a schematic circuit diagram of one alternative embodiment showing electronic circuitry interconnecting between a microprocessor control chip or PIC and various components, sensors, user input, cuing devices, pump activation, clinician input/output, and data transfer interfaces according to the present invention.

Figure 10A:
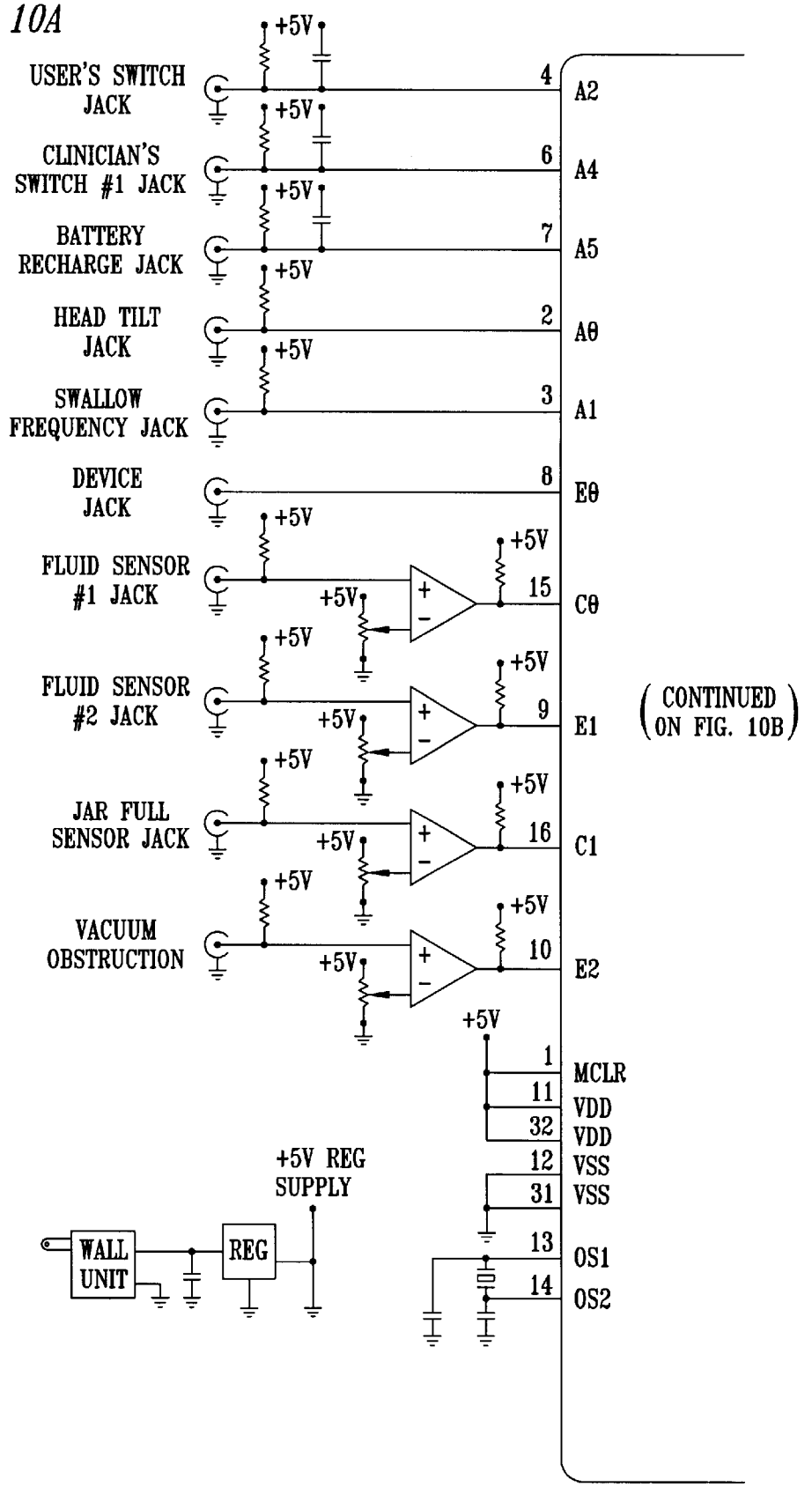
FIGS. 10A and 10B are detailed electronic circuitry and interconnection with the microprocessor chip for controlling the saliva compensation device elaborating in greater detail on the schematic of FIG. 9 according to the present invention.
Figure 10B:
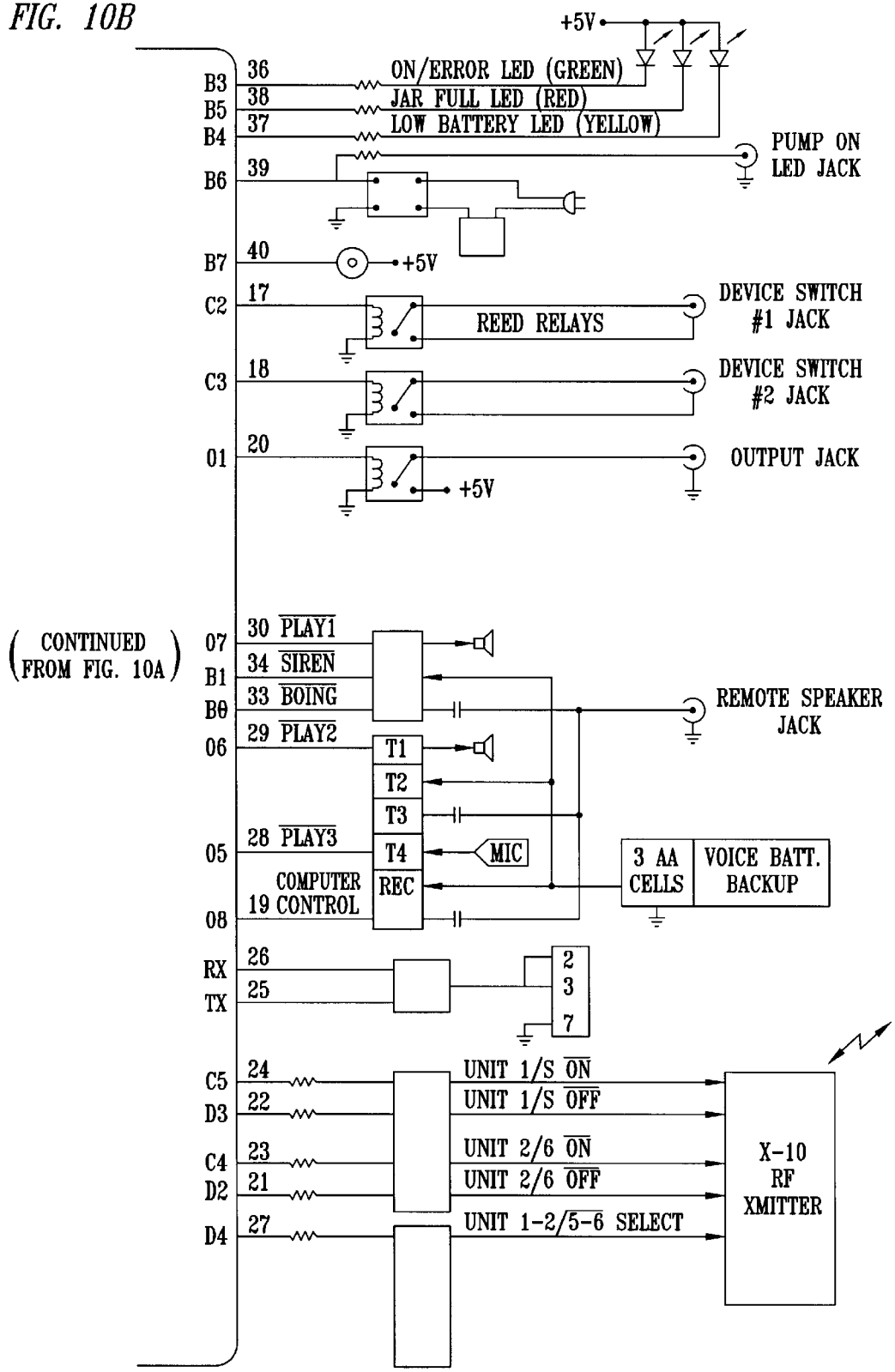

The embodiment depicted in FIGS. 10A and 10B includes two portions of a detailed electronic circuit diagram with circuitry interconnection with the microprocessor chip controlling the saliva compensation device according to the present invention. The specific features and values set forth are representative of the structural features of the invention and instructional to those skilled in the art. The specific components and values therefore are not intended to limit the scope of the invention as described and claimed.

Figure 11:
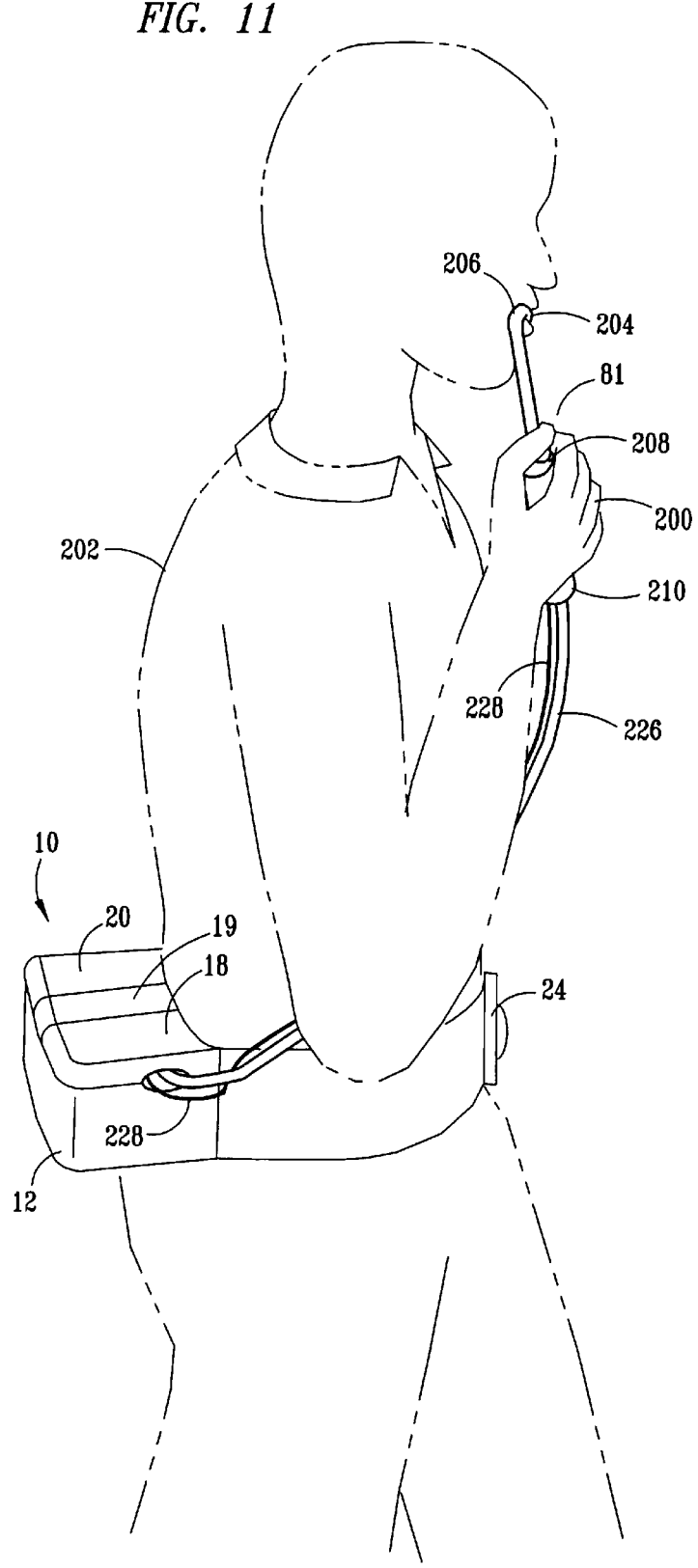
FIG. 11 is a perspective view of one embodiment of a handheld oral collector connected to the portable saliva collection device and being used by inserting a portion of the handheld collector into the user's mouth.

FIG. 11 is a perspective view of one embodiment of a handheld oral saliva collector 81 shown held in the hand 200 of a user (depicted in phantom lines). The handheld oral saliva collector 81 is operatively connected via hollow collection tube 226 and activation cable 228. The handheld oral saliva collection device 81 includes a portion 206 thereof that is insertable into a user's mouth 204. A switch 208 is provided on the handle 210 of the handheld oral saliva collection unit 81. By way of example, switch 208 may be a pushbutton switch 208a, as shown in FIG. 12, or alternatively may be a toggle switch 208b (not shown in FIG. 12, see example in FIG. 16) activatable between an "On" and an "Off" position by pushing the button for "On" and releasing the button for "Off" or by toggling the switch from the "On" to the "Off" position.

Figure 12:
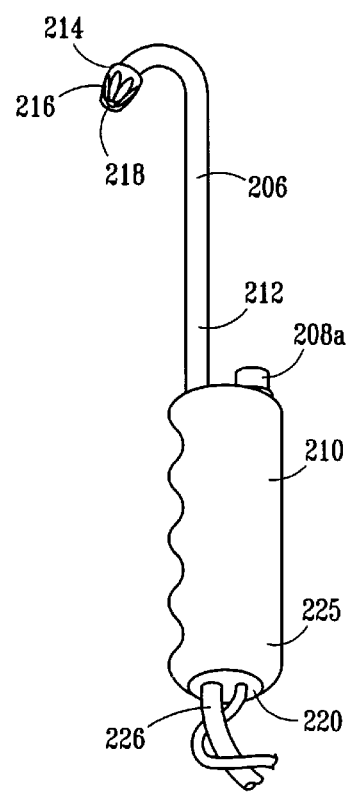
FIG. 12 is a perspective view of one embodiment of a handheld arm saliva collector.
Figure 13:
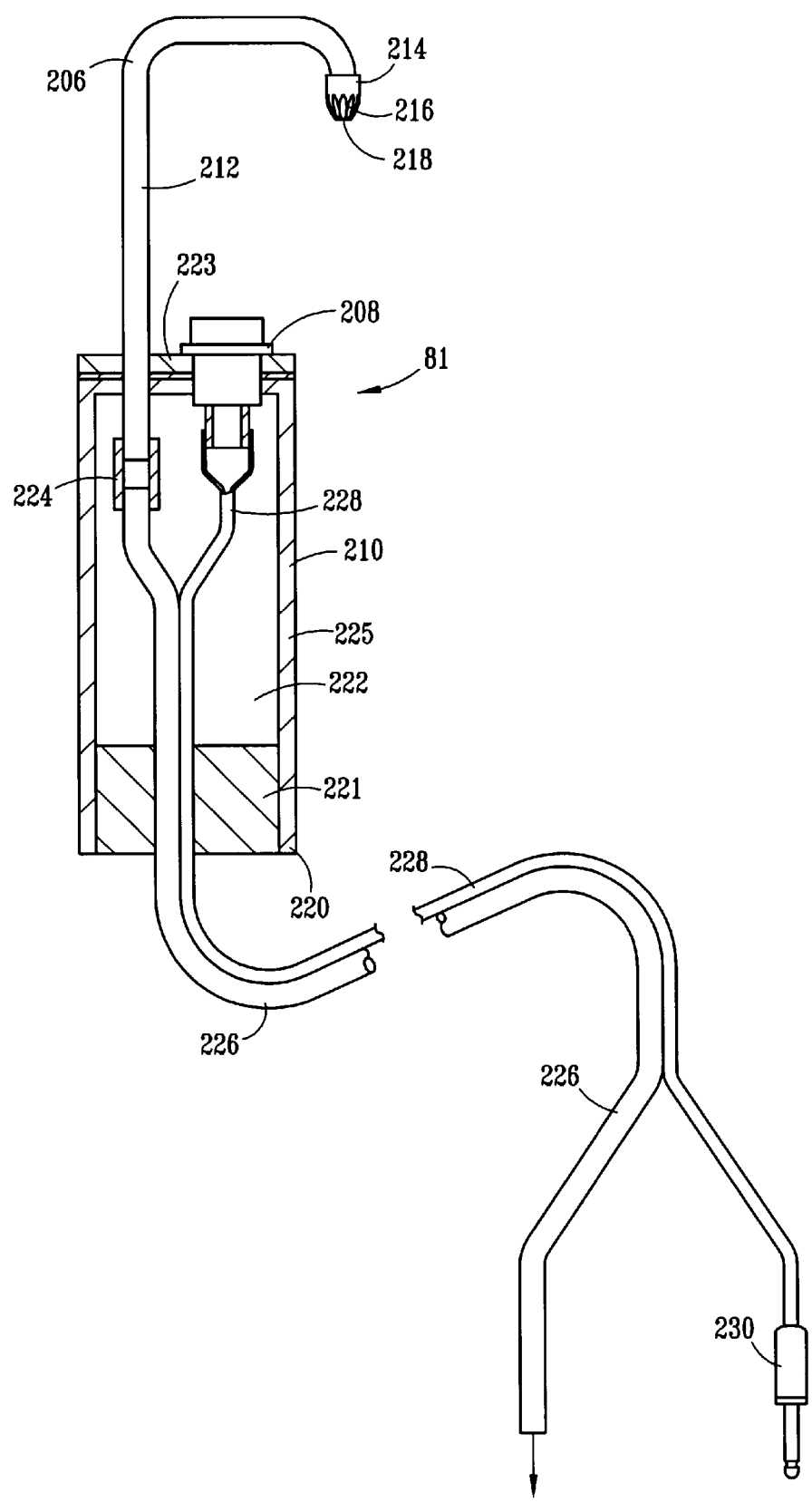
FIG. 13 is a schematic partial cross-sectional view of the handheld oral saliva collector of FIG. 12.

FIG. 12 shows a perspective view of the handheld oral saliva collection device of FIG. 11. Also, FIG. 13 depicts a schematic drawing of handle 210 shown in cross-section for enhanced understanding. In FIG. 12 it will be observed that the portion 206 insertable into the user's mouth includes a hollow tubular portion 212 interconnected with the hollow tube 226 for conveying collected saliva to the container unit 50 of FIG. 1. A suction head 214 is connected to the portion 206 insertable into the user's mouth. The suction head 214 may be constructed of a convenient size for attaching directly to tubular portion 212 or may be integrally formed with tubular portion 212. Suction head 214 is provided with a plurality of orifices or slits 216 such that the opening is partially blocked or shielded at 218. This permits fluids to be suctioned into the tube portion 212 while shielding the soft flesh of the mouth, tongue, lips and gums from being suctioned into the opening.

The handheld handle portion 210 has a body 220 preferably covered with a pliant surface 225. The body is sufficient rigidity to maintain the hand-holding shape of the handle 210, yet having a surface shaped for and sufficiently soft for comfortable holding and continuous carrying of the collection unit.

As will be more fully understood with reference to FIG. 13, which is a partial cross-sectional view of the handle portion of the handheld oral collection device 81, tubing portion 212 extends into the body 220 and is connected at 224 to hollow collection tube 226 to suction the saliva to the collection container of the portable saliva compensation device.

Further understanding may be had with reference to FIG. 13 showing the handheld collector 81 of FIG. 12, with the handle 210 shown in partial cross-section. The handle 210 includes a substantially rigid tubular portion 220 with a bottom-end portion 221 and a top-end portion 223 defining an interior volume 222. Within the interior volume 222, tubular portion 212 is connected to hollow tubing 226 as with a sealed cylindrical coupler 224. The switch 208 provides an electrical signal through pump activation cable 228. Activation cable 228 is provided with a plug-in connector 230 by which actuation of switch 208 is communicated to the pump unit 30 carried in carrying case 12 of FIG. 1 above.

In FIG. 14, an alternative embodiment of the handheld oral saliva collection unit 83, is shown in a perspective view. FIG. 15 also shows collection unit 83 of FIG. 14 in a schematic partial cross-sectional view. A handheld, flexible squeeze bulb 232 is provided connected to a portion 206 for insertion into the user's mouth. A tubular section 212 is coupled at a coupler 234 to the hollow tubing 226. Both tubular section 212 and hollow tubing 226 communicate through the exterior squeeze bulb 232 and are sealingly engaged at 234 and 236 with the squeeze bulb where the tubings 212 and 226 penetrate through the bulb 232 in order to maintain the internal chamber 244 substantially sealed from the outside environment. In this embodiment, the activation switch 242 comprises a pressure switch 242 and a pressure communication tube 240 extends sealingly through bulb 232 at a sealed entry 238. An open end 246 is thereby exposed to the internal volume 244. Upon squeezing the bulb 232, pressure inside chamber 244 increases and the increased pressure is communicated through pressure communication tube 240, thereby activating pressure switch 242. The activation of pressure switch 242 provides an electrical signal along activation cable 228 that is connectable with jack 230 to the electronic control portion of the hygienic saliva compensation pump device according to the present invention. In this embodiment, the user need not be capable of activating a button or toggle switch 208 (as in FIGS. 12 and 13) with a digital or thumb, but rather need only be capable of squeezing or otherwise causing pressure on squeeze bulb 232 in order to activate suction through suction head 214.

Figure 16:
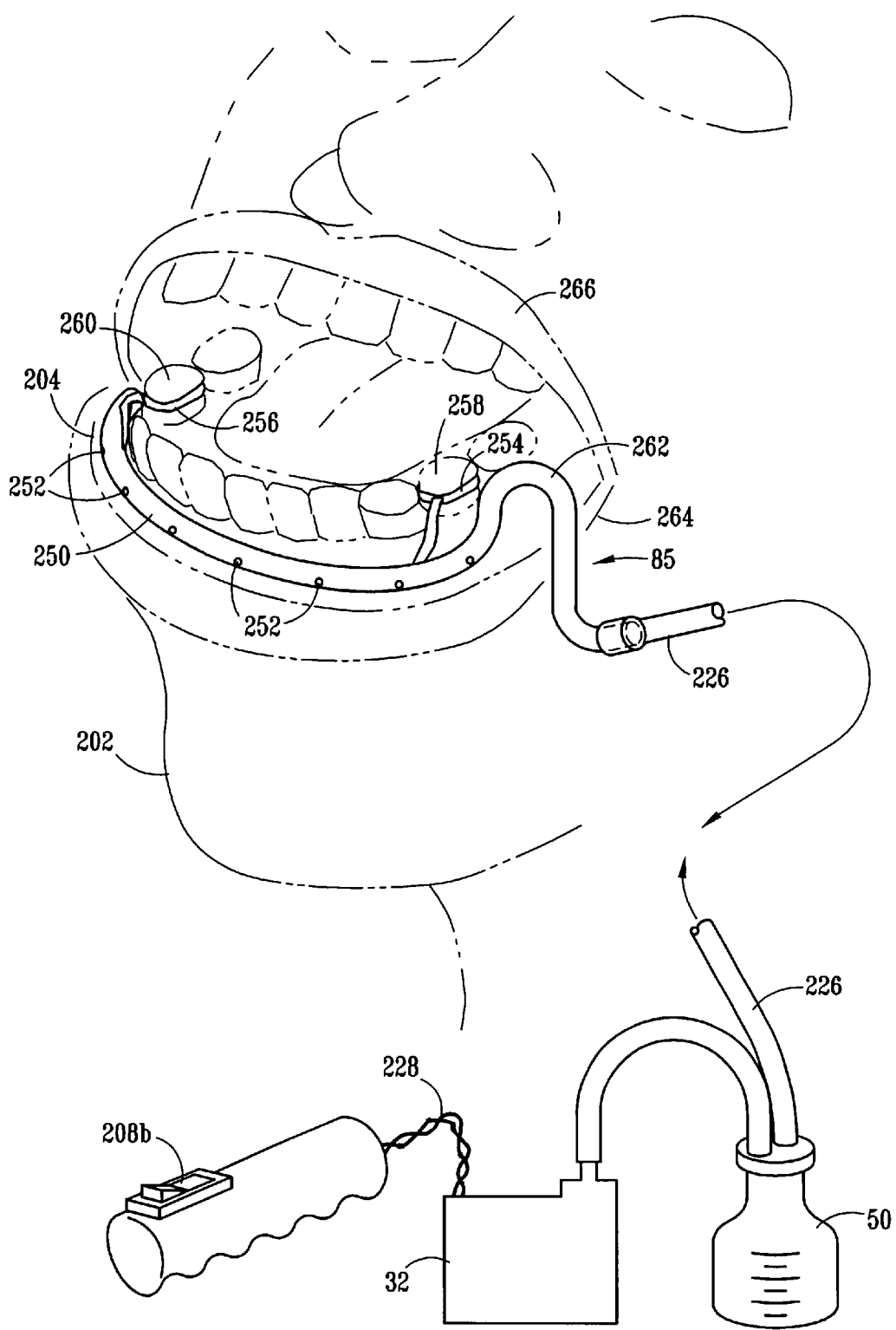
FIG. 16 is a schematic depiction of an intra-oral collector according to another aspect of the invention, shown with a portion thereof secured inside of the user's mouth (shown in phantom lines).

In an alternative embodiment of an intra-oral device 85 is depicted in a perspective view in FIG. 16 shown appropriately mounted in a user's mouth 204 (schematically depicted with phantom lines). The intra-oral collection unit 85 may be constructed with a curved collection tubing 250, having a plurality of orifices 252 formed through the wall of the tubing 250. Preferably, the curved tubing may be made of stainless steel or of a medical grade plastic capillary tube. In the embodiment in which curved collection tubing 250 is stainless steel, then preferably stainless steel molar connectors 254 and 256 act to hold the intra-oral saliva collection device in place, secured to molars 258 and 260, and fittingly curved around the lower gums. The curved tubing 250 is connected to collection tubing 226 using a connector tube 262 and thereby a collection container 50 and pump 32 for removing excess saliva directly from the user's mouth to avoid, or at least reduce, drooling. The connector tube 262 preferably rises above collection curved tubing 250 and exits between the lips 264 and 266 of the user 202. Activation may be by. handheld switch 208, such as a toggle switch 208b (as in FIG. 16) or a button 208a (FIG. 12 or 13). Activation may also be automatic and configureable, it may be preprogrammed and changeable.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A portable saliva compensation device comprising:
   a) a carrying case;
   b) a vacuum pump in said carrying case;
   c) a container in said carrying case;
   d) a portable power supply in said carrying case operatively connected to provide power to said vacuum pump;
   e) an electrical control circuit operatively connected to said portable power supply and to said pump;
   f) a saliva collection device having a portion thereof adapted to be positioned in a user's mouth for collecting excess saliva from the user's mouth;
   g) a hollow tube connecting between said saliva collection device and said container; and
   h) an activation device operatively coupled to said electrical control circuit to activate said vacuum pump to collect excess saliva from the user's mouth, thereby drawing said saliva from said mouth into said collection device through said hollow tube and into said container, wherein said activation device comprises:
      (i) a programable integrated circuit (PIC) in said electrical control circuit for controlling activation of said vacuum pump; and
      (ii) a communication port connected to said PIC for programming said PIC from a personal computer.

2. A portable saliva compensation device as in claim 1 wherein said communications port comprises a serial port.

3. A portable saliva compensation device as in claim 1 wherein said communications port comprises a parallel port.

4. A portable saliva compensation device as in claim 1 wherein said communications port comprises an infrared port.

5. A portable saliva compensation device comprising:
   a) a carrying case;
   b) a vacuum pump in said carrying case;
   c) a container in said carrying case, wherein said container further comprises a reservoir measuring device for determining the presence of one or more predetermined volumes of collected saliva;
   d) a portable power supply in said carrying case operatively connected to provide power to said vacuum pump;
   e) an electrical control circuit operatively connected to said portable power supply and to said pump;
   f) a saliva collection device having a portion thereof adapted to be positioned in a user's mouth for collecting excess saliva from the user's mouth;
   g) a hollow tube connecting between said saliva collection device and said container; and
   h) an activation device operatively coupled to said electrical control circuit to activate said vacuum pump to collect excess saliva from the user's mouth, thereby drawing said saliva from said mouth into said collection device through said hollow tube and into said container.

6. A portable saliva compensation device as in claim 5 wherein said reservoir measuring device comprises a scale formed on said container.

7. A portable saliva compensation device as in claim 5 wherein said reservoir measuring device further comprises an electronic liquid detection device attached in said container for determining one or more predetermined quantities of saliva in said container.

8. A portable saliva compensation device as in claim 7 wherein said predetermined levels detected comprise a minimum detectable level indicating the presence of saliva in said container and a maximum detectable level indicating that the container is full.

9. A portable saliva compensation device comprising:
   a) a carrying case;
   b) a vacuum pump in said carrying case;
   c) a container in said carrying case;
   d) a portable power supply in said carrying case operatively connected to provide power to said vacuum pump;
   e) an electrical control circuit operatively connected to said portable power supply and to said pump;
   f) a saliva collection device having a portion thereof adapted to be positioned in a user's mouth for collecting excess saliva from the user's mouth;
   g) a hollow tube connecting between said saliva collection device and said container;
   h) an activation device operatively coupled to said electrical control circuit to activate said vacuum pump to collect excess saliva from the user's mouth, thereby drawing said saliva from said mouth into said collection device through said hollow tube and into said container; and
   i) wherein said carrying case comprises a fanny pack having a belt for strapping said carrying case to a user for "hands-free" carrying.

10. A portable saliva compensation device comprising:
    a) a carrying case;
    b) a vacuum pump in said carrying case;
    c) a container in said carrying case;

d) a portable power supply in said carrying case operatively connected to provide power to said vacuum pump;

e) an electrical control circuit operatively connected to said portable power supply and to said pump;

f) a handheld saliva collector unit having a portion thereof adapted to be positioned in a user's mouth for collecting excess saliva from the user's mouth;

g) a hollow tube connecting between said saliva collector unit and said container;

h) an activation device operatively coupled to said electrical control circuit to activate said vacuum pump to collect excess saliva from the user's mouth, thereby drawing said saliva from said mouth into said saliva collector unit through said hollow tube and into said container; and i) wherein said handheld saliva collector unit further comprises a squeeze bulb from which said mouth insertion tube projects and wherein said activation device comprises a pressure switch sealingly coupled to said squeeze bulb to activate the pump upon squeezing said bulb.

11. A portable saliva compensation device comprising:

a) a carrying case;

b) a vacuum pump in said carrying case;

c) a container in said carrying case;

d) a portable power supply in said carrying case operatively connected to provide power to said vacuum pump;

e) an electrical control circuit operatively connected to said portable power supply and to said pump;

f) a saliva collection device having a portion thereof adapted to be positioned in a user's mouth for collecting excess saliva from the user's mouth;

g) a hollow tube connecting between said saliva collection device and said container; and h) an activation device operatively coupled to said electrical control circuit to activate said vacuum pump to collect excess saliva from the user's mouth, thereby drawing said saliva from said mouth into said collection device through said hollow tube and into said container; and i) a data recordation circuit connected to said control circuit.

12. A portable saliva compensation device as in claim 11 further comprising a data transfer device by which recorded data may be transferred to a remote device such as a PC.

13. A portable saliva compensation device comprising:

a) a carrying case;

b) a vacuum pump in said carrying case;

c) a container in said carrying case;

d) a portable power supply in said carrying case operatively connected to provide power to said vacuum pump;

e) an electrical control circuit operatively connected to said portable power supply and to said pump, wherein said electronic control is programmable to detect one or more predetermined activities or conditions of the user, of the pump, the container, and of the saliva collection activation switch;

f) a saliva collection device having a portion thereof adapted to be positioned in a user's mouth for collecting excess saliva from the user's mouth;

g) a hollow tube connecting between said saliva collection device and said container; and h) an activation device operatively coupled to said electrical control circuit to activate said vacuum pump to collect excess saliva from the user's mouth, thereby drawing said saliva from said mouth into said collection device through said hollow tube and into said container.

14. A portable saliva compensation device as in claim 13 wherein said one or more predetermined activities are selected from a group of activities comprising head tilting, head positioning, swallowing and swallow frequency.

15. An intra-oral saliva collector unit for use with a portable pump and saliva collection container, said intra-oral collector unit comprising;

a) a thin, curved collection tube having orifices formed therein for placement in a user's mouth, curved along and adjacent to the user's lower gum;

b) a thin connection tube extending from said curved collection tube upward and outward from between the user's lips;

c) a hollow tubing adapted to be coupled between said thin connection tubing and said portable saliva collection container and pump to provide fluid communication therebetween;

d) an activation switch connectable to said pump for selectively activating or deactivating the pump to suction saliva from said user's mouth; and e) an automatic control circuit for activating said pump upon detection of a predetermined amount of saliva and for timing the continued activation for a predetermined time after said detection of saliva.

* * * * *

UNITED STATES PATENT AND TRADEMARK OFFICE
CERTIFICATE OF CORRECTION

PATENT NO. : 6,652,481 B1 Page 1 of 1
DATED : November 25, 2003
INVENTOR(S) : Brown et al.

It is certified that error appears in the above-identified patent and that said Letters Patent is hereby corrected as shown below:

<u>Title page,</u>
Item [75], Inventors, should read as follows:
-- [75] Inventors: Carrie Brown, Dallas, TX (US);
                  Lorton Trent, McKinney, TX (US);
                  Jack Atkinson, Southlake, TX (US);
                  Janet H. Allaire, Charlottesville, VA (US);
                  Eric Frische, Chandler, AZ (US);
                  Richard Adams, Plano, TX (US);
                  Stan Richardson, Dallas, TX (British) --

Signed and Sealed this

Thirtieth Day of March, 2004

JON W. DUDAS
*Acting Director of the United States Patent and Trademark Office*